(12) United States Patent
Ewers et al.

(10) Patent No.: US 10,206,571 B2
(45) Date of Patent: Feb. 19, 2019

(54) APPARATUS, SYSTEMS, AND METHODS FOR TREATING OBSTRUCTIVE SLEEP APNEA

(71) Applicant: Fresca Medical Inc., San Clemente, CA (US)

(72) Inventors: Richard Ewers, Fullerton, CA (US); Kevin Chen, Palos Verdes Estates, CA (US); Andrew Dominguez, San Clemente, CA (US)

(73) Assignee: Fresca Medical, Inc., San Clemente, CA (US)

( * ) Notice: Subject to any disclaimer, the term of this patent is extended or adjusted under 35 U.S.C. 154(b) by 0 days.

(21) Appl. No.: 15/334,243

(22) Filed: Oct. 25, 2016

(65) Prior Publication Data

US 2017/0157356 A1    Jun. 8, 2017

Related U.S. Application Data

(63) Continuation of application No. 14/930,284, filed on Nov. 2, 2015, now Pat. No. 9,492,086.

(Continued)

(51) Int. Cl.
*A61M 16/08* (2006.01)
*A61B 5/00* (2006.01)
(Continued)

(52) U.S. Cl.
CPC .......... *A61B 5/0002* (2013.01); *A61B 5/4809* (2013.01); *A61B 5/4812* (2013.01);
(Continued)

(58) Field of Classification Search
CPC ....... A61B 5/11; A61B 5/4809; A61B 5/4818; A61B 5/4836; A61M 16/0051; A61M 16/0057; A61M 16/0066; A61M 16/0069; A61M 16/06; A61M 16/0683; A61M 16/0688; A61M 16/0816; A61M 16/0825; A61M 16/0833; A61M 16/0866; A61M 16/0875; A61M 16/1055; A61M 16/107; A61M 16/1075; A61M 16/16; A61M 16/161; A61M 16/201; A61M 16/202; A61M 16/206; A61M 16/208; A61M 16/209; A61M 2016/0027; A61M 2016/0033; A61M 2016/0039; A61M 2016/0661; A61M 2039/1027; A61M 2039/1038; A61M 2039/1044; A61M 2205/0222; A61M 2205/0238;
(Continued)

(56) References Cited

U.S. PATENT DOCUMENTS

| | | |
|---|---|---|
| 3,419,031 A | 12/1968 | Hesse |
| 3,556,122 A | 1/1971 | Laerdal |

(Continued)

*Primary Examiner* — Annette Dixon
(74) *Attorney, Agent, or Firm* — Manuel de la Cerra

(57) ABSTRACT

Apparatus, systems, and methods are provided for treating obstructive sleep apnea. A CPAP system with an integrated oximeter sensor is disclosed wherein the sensor communicates with an oximeter processor that controls the blower. A nasal air flow sensor may also be incorporated that provides more data to the processor. A unique lightweight, flexible and stretchable hose for CPAP systems is also disclosed. The hose may have a magnetic connection with the blower.

22 Claims, 10 Drawing Sheets

Related U.S. Application Data

(60) Provisional application No. 62/246,339, filed on Oct. 26, 2015, provisional application No. 62/246,489, filed on Oct. 26, 2015, provisional application No. 62/246,328, filed on Oct. 26, 2015, provisional application No. 62/246,477, filed on Oct. 26, 2015, provisional application No. 62/275,899, filed on Jan. 7, 2016, provisional application No. 62/311,804, filed on Mar. 22, 2016, provisional application No. 62/382,980, filed on Sep. 2, 2016, provisional application No. 62/382,988, filed on Sep. 2, 2016.

(51) Int. Cl.

| | | |
|---|---|---|
| *A61M 16/06* | (2006.01) | |
| *A61M 16/00* | (2006.01) | |
| *A61M 16/20* | (2006.01) | |
| *A61B 5/01* | (2006.01) | |
| *A61B 5/024* | (2006.01) | |
| *A61B 5/053* | (2006.01) | |
| *A61B 5/08* | (2006.01) | |
| *A61B 5/11* | (2006.01) | |

(52) U.S. Cl.
CPC .... *A61M 16/0057* (2013.01); *A61M 16/0069* (2014.02); *A61M 16/024* (2017.08); *A61M 16/06* (2013.01); *A61M 16/0666* (2013.01); *A61M 16/0816* (2013.01); *A61M 16/0875* (2013.01); *A61M 16/206* (2014.02); *A61M 16/208* (2013.01); *A61B 5/01* (2013.01); *A61B 5/02405* (2013.01); *A61B 5/02438* (2013.01); *A61B 5/0533* (2013.01); *A61B 5/0816* (2013.01); *A61B 5/1118* (2013.01); *A61M 2016/003* (2013.01); *A61M 2205/128* (2013.01); *A61M 2205/3569* (2013.01); *A61M 2205/3592* (2013.01); *A61M 2205/50* (2013.01); *A61M 2230/005* (2013.01); *A61M 2230/205* (2013.01); *A61M 2230/63* (2013.01)

(58) Field of Classification Search
CPC .......... A61M 2205/14; A61M 2205/18; A61M 2205/3368; A61M 2205/3375; A61M 2205/3553; A61M 2205/3561; A61M 2205/3584; A61M 2205/3592; A61M 2205/42; A61M 2205/505; A61M 2205/52; A61M 2205/583; A61M 2205/6054; A61M 2205/8206; A61M 2205/8237; A61M 2205/8281; A61M 2209/06; A61M 2209/08; A61M 2209/088; A61M 2230/04; A61M 2230/18; A61M 2230/205; A61M 2230/63; A61M 39/1011; A62B 9/04; F16L 37/004; Y10T 29/49412; Y10T 29/49826
USPC ............ 128/200.24, 202.27, 204.18, 204.19, 128/204.21, 204.23, 205.18, 205.23, 128/205.24
See application file for complete search history.

(56) References Cited

U.S. PATENT DOCUMENTS

| | | | |
|---|---|---|---|
| 3,978,878 A | | 9/1976 | Rudolph |
| 4,190,088 A | * | 2/1980 | Lalikos .................. F16L 11/12 138/104 |
| 4,239,038 A | | 12/1980 | Holmes |
| 4,373,520 A | | 2/1983 | Arbique |
| 4,428,392 A | | 1/1984 | Jones et al. |
| 5,002,050 A | | 3/1991 | McGinnis |
| 5,005,568 A | | 4/1991 | Loescher et al. |
| 5,647,355 A | | 7/1997 | Starr et al. |
| 6,306,114 B1 | | 10/2001 | Freeman et al. |
| 6,349,724 B1 | * | 2/2002 | Burton .............. A61M 16/0057 128/204.18 |
| 7,793,987 B1 | * | 9/2010 | Busch ............... A61M 16/0816 285/9.1 |
| 9,144,653 B2 | | 9/2015 | Chalvignac |
| 2002/0170562 A1 | | 11/2002 | Lurie et al. |
| 2002/0195105 A1 | | 12/2002 | Blue et al. |
| 2004/0099266 A1 | | 5/2004 | Cross et al. |
| 2008/0264413 A1 | * | 10/2008 | Doherty .............. A61M 16/021 128/202.27 |
| 2009/0032022 A1 | | 2/2009 | Ho et al. |
| 2014/0246024 A1 | * | 9/2014 | Cragg ................. A61M 16/208 128/204.19 |
| 2014/0246025 A1 | * | 9/2014 | Cragg ................. A61M 16/208 128/204.19 |

* cited by examiner

POSITIVE INDICATION OF APNEA EVENT

INDETERMINATE INDICATION OF APNEA EVENT

NEGATIVE INDICATION OF APNEA EVENT

APPARATUS, SYSTEMS, AND METHODS FOR TREATING OBSTRUCTIVE SLEEP APNEA

1.0 TECHNICAL FIELD

The present invention is related to medical systems, devices, and methods. More specifically, the invention is related to systems, devices and methods for treating obstructive sleep apnea or snoring.

2.0 RELATED APPLICATIONS

This application claims priority as the non-provisional of U.S. Provisional Application No. 62/246,339 filed Oct. 26, 2015 titled "VENTING OF A VALVED CPAP MASK TO CREATE A COMFORTABLE BREATHING SENSATION," as the non-provisional of U.S. Provisional Application No. 62/246,489 filed Oct. 26, 2015 titled "MANAGING SLEEP APNEA WITH PULSE OXIMETERS AND WITH ADDITIONAL ASSESSMENT TOOLS," as the non-provisional U.S. Provisional Application No. 62/246,328 filed Oct. 26, 2015 titled "NOVEL LOW FLOW TECHNOLOGY DESIGNED TO MEET CPAP EFFICACY," and as the non-provisional U.S. Provisional Application No. 62/246,477 filed Oct. 26, 2015 titled "COMPOSITE CONSTRUCTION AIR DELIVERY HOSE FOR USE WITH CPAP TREATMENT"; all of which are assigned to the same assignee as the present application and are hereby incorporated by reference in their entirety. This application claims priority as a continuation of U.S. application Ser. No. 14/930,284 titled "APPARATUS, SYSTEMS, AND METHODS FOR TREATING OBSTRUCTIVE SLEEP APNEA" filed on Nov. 2, 2015; which is assigned to the same assignee as the present application and are hereby incorporated by reference in its entirety.

In addition, this application is related to U.S. patent application Ser. No. 14/278,587, filed May 15, 2014, titled "AUTO-FEEDBACK VALVE FOR A SLEEP APNEA DEVICE," U.S. patent application Ser. No. 13/860,926, filed Apr. 11, 2013, titled "SLEEP APNEA DEVICE," U.S. Provisional Application Ser. No. 61/623,855, filed Apr. 13, 2012, titled "SLEEP APNEA DEVICE," U.S. Provisional Application Ser. No. 61/775,430, filed Mar. 8, 2013, titled "SLEEP APNEA DEVICE," U.S. Provisional Application No. 61/823,553, filed May 15, 2013, titled "SLEEP APNEA DEVICE," U.S. Provisional Application No. 61/838,191, filed Jun. 21, 2013, titled "SLEEP APNEA DEVICE," U.S. Provisional Application No. 61/962,501, filed Nov. 8, 2013, titled "SLEEP APNEA DEVICE," U.S. Provisional Application No. 61/909,956, filed Nov. 27, 2013, titled "SLEEP APNEA DEVICE," U.S. Provisional Application No. 61/927,355, filed Jan. 14, 2014, titled "VALVE WITH PRESSURE FEEDBACK," U.S. Provisional Application No. 62/134,506 filed Mar. 17, 2015 titled "VALVE WITH PRESSURE FEEDBACK DRAFT PROVISIONAL APPLICATION," U.S. Provisional Application No. 62/163,601, filed May 19, 2015, titled "AIRFLOW GENERATOR WITH DELAYED ONSET", U.S. Provisional Application No. 62/184,787 filed Jun. 25, 2015 titled "SLEEP APNEA DEVICE," and U.S. Provisional Application No. 62/239,146 filed Oct. 8, 2015 titled "SLEEP APNEA DEVICE," U.S. Provisional Application No. 62/275,899 filed Jan. 7, 2016 titled "VALVED MASK TO REDUCE AND PREVENT SNORING", U.S. Provisional Application No. 62/311,804 filed Mar. 22, 2016 titled "IMPROVEMENTS TO SLEEP APNEA MACHINE", U.S. Provisional Application No. 62/382,980 filed Sep. 2, 2016 titled "DUAL ROTATABLE HOSE FOR USE WITH CPAP TREATMENT"; and U.S. Provisional Application No. 62/382,988 filed Sep. 2, 2016 titled "NASAL PILLOW AND HEAD GEAR FOR USE WITH CPAP TREATMENT" all of which are assigned to the same assignee as the present application and are hereby incorporated by reference in their entirety.

2.0 BACKGROUND

Obstructive sleep apnea (OSA) is a common medical disorder that can be quite serious. It has been reported that approximately one in twenty-two Americans (about 12,000,000 people) suffer from OSA, and many cases go undiagnosed. Chronic fatigue has long been recognized as the hallmark of OSA, but more recently, large clinical studies have shown a strong link between OSA, strokes and death.

Obstructive sleep apnea is a condition in which the flow of air pauses or decreases during breathing while one is asleep, because the airway has become narrowed, blocked, or floppy. A pause in breathing is called an apnea episode, while a decrease in airflow during breathing is called a hypopnea episode. Almost everyone has brief apnea or hypopnea episodes while they sleep. In OSA, however, apnea episodes occur more frequently and last longer than in the general population. OSA has become an increasingly costly medical condition in recent years, as the disorder is more prevalent in obese people and obesity has become significantly more prevalent. Unfortunately, the currently available options for treating OSA are not ideal.

A person with OSA usually begins snoring heavily soon after falling asleep. Often the snoring gets louder. The snoring is then interrupted by a long silent period during which there is no breathing. This is followed by a loud snort and gasp, as the person attempts to breathe. This pattern repeats. Many people wake up unrefreshed in the morning and feel sleepy or drowsy throughout the day. This is called excessive daytime sleepiness (EDS). People with sleep apnea may act grumpy or irritable, be forgetful, fall asleep while working, reading, or watching TV, feel sleepy or even fall asleep while driving, or have hard-to-treat headaches. OSA sufferers may also experience depression that becomes worse, hyperactive behavior (especially in children), or leg swelling (if severe).

The most widely used therapy for OSA is Continuous Positive Airway Pressure (CPAP). A CPAP system typically consists of a mask fitting in or over the nose or nose and mouth, an air pressurizing console (or blower) and a hose connecting the two (typically a six-foot long hose with a 20 mm diameter bore). CPAP works by pressurizing the upper airway throughout the breathing cycle, essentially inflating the airway to keep it open and thus creating what is sometimes referred to as a "pneumatic splint." This flow is at set pressure that has been predetermined through medical testing to be appropriate to create a pneumatic splint in the user's airway. This prevents airway collapse and allows the user to breath without obstruction. Because the masks typically leak air, CPAP systems have to provide an airflow rate of up to 200 liters per minute (approximate figure based on unpublished data). The high airflow rate is needed for multiple reasons. First, all the air needed for breathing must come through the hose. Second, conventional masks have an intended leak built in for the purpose of constant "$CO_2$ washout." Third, these systems achieve the required pressure by using a high airflow rate to generate a back-pressure at the mask end where the air is leaking out. Unfortunately, this high flow rate makes breathing feel quite uncomfortable for many users and requires a relatively large, noisy blower. Additionally, the high required flow rates of CPAP often cause discomfort during exhalation due to increased resistance, as well as nasal dryness, dry mouth, ear pain, rhinitis, abdominal bloating and headaches.

The overwhelming shortcoming of CPAP is poor user compliance. Over half of all users who try CPAP stop using it. Users dislike the side effects mentioned above, as well as having to wear an uncomfortable, claustrophobic mask, being tethered to a pressurizing console, the noise of the console, traveling with a bulky device, and a loss of personal space in bed.

Many CPAP devices and alternatives to CPAP have been developed, but all have significant shortcomings. Less invasive attempts at OSA treatment, such as behavior modification, sleep positioning and removable splints to be worn in the mouth, rarely work. A number of different surgical approaches for treating OSA have also been tried, some of which are still in use. For example, Uvulopalatopharyngoplasty (UPPP) and Laser Assisted Uvula Palatoplasty (LAUP) are currently used. Surgical approaches, however, are often quite invasive and not always effective at treating OSA.

One alternative approach to OSA treatment is to provide a pneumatic splint during the expiratory portion of the respiratory cycle by producing a partial blockage in the nose or mouth, thus slowing the release of air during expiration and increasing positive pressure in the airway. The simplest way to form an expiratory pneumatic splint, pursing the lips, has been shown to open the upper airway and improve breathing in emphysema users. This type of maneuver is generically labeled Expiratory Positive Airway Pressure (EPAP).

Therefore, it would be advantageous to have improved systems, devices and methods for treating OSA and snoring. Ideally, such systems, devices and methods would be less cumbersome than currently available CPAP systems, to improve user compliance. Also ideally, such systems, devices and methods would provide some of the advantages of an expiratory pneumatic splint. At least some of these objectives were met by the embodiments described in references listed above and incorporated herein by reference.

While these references are an important improvement over the state of the art, it would be advantageous to improve upon these systems by making the system simpler and more compact in design, simpler to use, and more robust.

3.0 SUMMARY

The following presents a simplified summary in order to provide a basic understanding of some aspects of the claimed subject matter. This summary is not an extensive overview, and is not intended to identify key/critical elements or to delineate the scope of the claimed subject matter. Its purpose is to present some concepts in a simplified form as a prelude to the more detailed description that is presented later.

Provided in various example embodiments is an improved apparatus, system, and method for treating obstructive sleep apnea. In some embodiments holes are placed into the mask to relieve pressure.

In yet other embodiments, an oximeter (or oximetry sensor) is added to the systems to detect the oxygen level in the patient's blood, which can indicate the presence of an apnea event. The sensor may be wired or wireless and communicated the detected oxygen levels to an oximetry processor. The processor may be wired to the blower, or communicated with the blower wirelessly. Alternatively the blower may have the processor integrated. The processor can activate and control the blower to more effectively treat a patient suffering from sleep apnea.

In yet another embodiment, the mask may also include a nasal flow sensor that detects the flow of air. That sensor may be connected to the processor.

A novel, lightweight and flexible blower hose is disclosed. The hose has a low weight/length ratio, which is less cumbersome and convenient for the user. In addition, the small bend radius and high droop percentage signifies a high flexibility of the hose, which allows for an increased range of motion for the user. The hose can readily stretch with tensile loads, which is a useful for decoupling tensile loads due to force on the hose. A novel magnetic hose coupling device is also disclosed.

Additional aspects, alternatives and variations as would be apparent to persons of skill in the art are also disclosed herein and are specifically contemplated as included as part of the invention. The invention is set forth only in the claims as allowed by the patent office in this or related applications, and the following summary descriptions of certain examples are not in any way to limit, define or otherwise establish the scope of legal protection.

4.0 BRIEF DESCRIPTION OF THE DRAWINGS

Various embodiments are depicted in the accompanying drawings for illustrative purposes, and should in no way be interpreted as limiting the scope of the embodiments. Furthermore, various features of different disclosed embodiments can be combined to form additional embodiments, which are part of this disclosure. It will be understood that certain components and details may not appear in the figures to assist in more clearly describing the invention.

5.0 DETAILED DESCRIPTION OF EXAMPLE EMBODIMENTS

Figure 1:
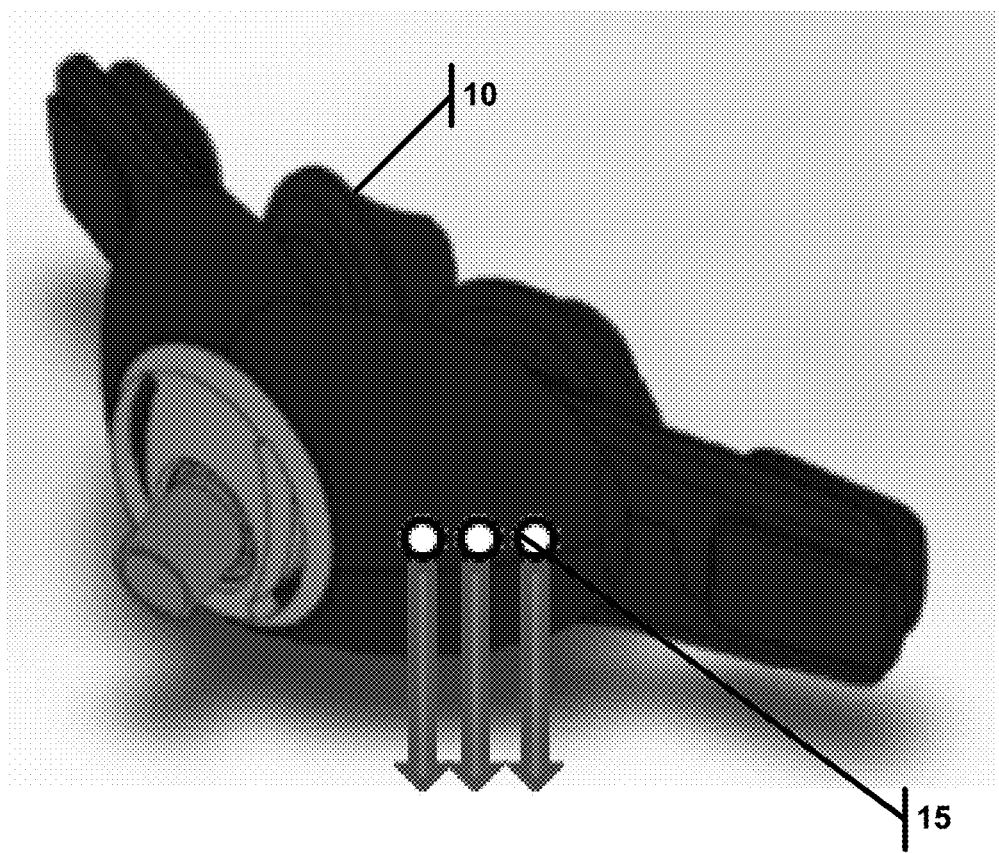
FIG. 1 illustrates a sleep CPAP mask with hole to relieve pressure.

Reference is made herein to some specific examples of the present invention, including any best modes contemplated by the inventor for carrying out the invention. Examples of these specific embodiments are illustrated in the accompanying figures. While the invention is described in conjunction with these specific embodiments, it will be understood that it is not intended to limit the invention to the described or illustrated embodiments. To the contrary, it is intended to cover alternatives, modifications, and equivalents as may be included within the spirit and scope of the invention as defined by the appended claims.

In the following description, numerous specific details are set forth in order to provide a thorough understanding of the present invention. Particular example embodiments of the present invention may be implemented without some or all of these specific details. In other instances, process operations well known to persons of skill in the art have not been described in detail in order not to obscure unnecessarily the present invention. Various techniques and mechanisms of the present invention will sometimes be described in singular form for clarity. However, it should be noted that some embodiments include multiple iterations of a technique or multiple mechanisms unless noted otherwise. Similarly, various steps of the methods shown and described herein are not necessarily performed in the order indicated, or performed at all in certain embodiments. Accordingly, some implementations of the methods discussed herein may include more or fewer steps than those shown or described. Further, the techniques and mechanisms of the present invention will sometimes describe a connection, relationship or communication between two or more entities. It should be noted that a connection or relationship between entities does not necessarily mean a direct, unimpeded connection, as a variety of other entities or processes may reside or occur between any two entities. Consequently, an indicated connection does not necessarily mean a direct, unimpeded connection unless otherwise noted.

The following list of example features corresponds with FIGS. 1-11 and is provided for ease of reference, where like reference numerals designate corresponding features throughout the specification and figures:

Sleep apnea mask 10
Holes 15
Blower 20
Hose 25
Patient 30
Oximeter sensor 35
Oximeter processor 40
Wired connection from oximeter sensor to processor 45
Wired connection from oximeter processor to blower 50
Wireless connection from oximeter processor to blower 55
Blower with integrated oximeter processor 60
Wireless connection from oximeter sensor to processor 65
Mask with integrated oximeter sensor 70
Wired connection from mask with integrated oximeter sensor to processor 75
Wireless connection from mask with integrated oximeter sensor to processor 80
Mask with integrated nasal air flow sensor 85
Wired connection from mask with integrated nasal air flow sensor to processor 90
Elbow mask connection 95
Hose blower connector/magnet assembly 100
Blower magnet assembly 105
Oximetry data use method 900 (comprised of steps 902-965)
The attractive force between the hose magnet assembly and the blower magnet assembly 110
Hose Assembly Connector 111
Blower Assembly Connector 112
Post 115
Hinges 113a, 113b
Channel/Collar 116
Hinge Long Side 120
Hinge Short Side 125
Hinge End 130
Magnet 135
Hose Assembly Connector 136
Blower Assembly Connector 137
Retainer 140
Physical Connection 145
Interior Hole 150
Tapered End 155

5.1 Venting of a Valved CPAP Mask to Create a Comfortable Breathing Sensation

This disclosure is related to the exhalation state of the breathing cycle and in particular to the moments just prior to end of exhalation. At this particular time a patient has completed exhalation up to the point when the exhalation pressure drops below the set pressure of the exhalation valve. As designed the exhalation valve closes and block airflow out of the mask. This may cause the sensation of abrupt stoppage of flow to the sensitive receptors in the nose.

A way to mitigate this is to maintain even a trace amount of exhausting flow from the mask. This is intended to provide some sensation of flowing air even with the mask valves closed. What is considered in this invention is incorporating an intended leak in the FRESCA system by placing a small hole or set of small holes in the valve or mask body. These holes would be sized small enough so as not to allow so much exhaust that the mask cannot achieve pressure. In one embodiment, shown in FIG. 1, the sleep apena mask 10 would have a set of holes 15 on left and right forward facing surface of the mask. The holes 15 can be sized to allow a continuous exhaust of air between 0% and 50% of the flow from the blower at any given blower pressure setting.

5.2 Managing Sleep Apnea with Pulse Oximeters and with Additional Assessment Tools Pulse oximetry sensors could also be combined with additional measurements or historic patient data to optimize the detection and activation of treatment. Pulse oximetry, along with a clinical score, is an effective screening tool for sleep apnea. This approach, though not as accurate as polysomnography, is much simpler, low cost and can be done at home by the patient.

Polysomnography is performed in a sleep laboratory and a patient is required to stay overnight. The test monitors various physiological factors during sleep, including brain electrical activity, eye and jaw muscle movement, leg muscle movement, airflow, respiratory effort, EKG, and oxygen saturation. These tests are to determine the frequency of apneas during sleep and the body's reaction to the sleep apnea.

Apnea-hypopnea index, or AHI, is an index used to assess the severity of sleep apnea based on the total number of complete cessations (apnea) and partial obstructions (hypopnea) of breathing occurring per hour of sleep. These pauses in breathing must last for 10 seconds and are associated with a decrease in oxygenation of the blood. In general, the AHI can be used to classify the severity of disease (mild 5-15, moderate 15-30, and severe greater than 30).

According to a sleep apnea screening study performed by Adrian Williams and his colleagues, positive oximeter readings will show the existence of sleep apnea; together with a clinical score, false negatives can be drastically reduced. False-negatives can largely be explained by their less sever disease, as evidenced by fewer and shorter apneas. The study concluded that patients with positive oximeter readings or clinical scores of 3 or higher would indicate the presence of sleep apnea. The researchers also recommended repeating the pulse oximeter measurements over multiple nights to increase the accuracy. Other criterion for screening sleep apnea using clinical data were studied and published. The studies had shown encouraging results.

The clinical score consists of five components and each component has a score of one. These components are:
1. Loud and habitual snoring
2. Interrupted breathing
3. Excessive daytime sleepiness
4. Body mass index greater than 25
5. Use of hypotensive medications or blood pressure greater or equal to 140/90

The first two components are as reported by patient's spouse or family members. Examples of excess daytime sleepiness are: napping while driving, and difficulty in staying awake. One can also use the Epworth Sleepiness Scale. The final clinical score is obtained by adding all the scores with a possible maximum of five.

Pulse oximeter readings can be obtained with a wrist, toe, finger, shoulder, ear or handheld pulse oximeter which can take measurements continuously over the night. The readings follow three different patterns:
1. Positive: Cyclical changes with significant oxygen saturation changes
2. Negative: Steady readings with little variations during the entire sleep
3. Indeterminate: Frequent fluctuation within 4% range regardless of level of saturation Significant oxygen saturation change is defined as a drop in oxygen saturation of greater or equal to 4% and to a level of 90% or below. Each series of changes represents an apnea episode.

Research has shown that obstructive sleep apnea also changes heart rate dynamics. During periods of prolonged obstructive sleep apnea, the heart rate typically shows cyclic fluctuation associated with the apneic phase and the resumption of breathing. By analyzing the heart rate, a study has shown that obstructive sleep apnea could be detected in over 93% of the test cases.

Commercially available CPAP and APAP blower boxes use the monitoring of flow and pressure to determine corresponding apnea events (anomalies to flow and pressure). Various manufacturers use different algorithms to analyze the pressure and flow data for determination of sleep disorder. Significant effort has been conducted to optimize and create proprietary algorithms. There is some complication in doing this because the indicative flow and pressure events are being sensed at opposite ends of a typically six foot air supply hose. This may not be an ideal way to detect sleep disorders due to the complications of sensing for sleep disorders remote from the patient. Additionally, alternative technologies may have different pressure flow characteristics where conventional sensing algorithms may not work. Additionally new CPAP technologies may make sensing with flow and pressure more difficult.

FRESCA Medical has created a novel sleep apnea treatment mask and hose. It utilizes a set of valves and a smaller caliber air supply hose to create positive pressure treatment in a new manner that has benefits for patient use and comfort. These devices are claimed and described in the patent applications listed above. FRESCA now discloses utilizing a "closed loop" detection and response system for the treatment of OSA (Obstructive Sleep Apnea).

The proposed invention may utilize a conventional CPAP treatment mask and hose or FRESCA's novel CPAP treatment mask and hose or any CPAP treatment mask and hose with a blower box designed to incorporate pulse oximetry data for the detection of sleep disorders. In one embodiment the patient adorns the CPAP treatment mask and hose, additionally they attach a pulse oximetry measurement device. There are various pulse oximetry devices.

By way of example consider a device that attaches to a fingertip and has a wired communication to a processor. This wired communication could interface with a standalone pulse oximetry processor or could wirelessly communicate with the pulse oximetry processor. This processor could be in wired or wireless communication with a CPAP blower designed to accept pulse oximetry signals. This particular CPAP blower would monitor the pulse oximetry data as described in the literature, and shown in FIG. 5. The oximetry data follows three patterns: (1) Positive: Cyclical changes with significant oxygen saturation changes; (2) Negative: Steady readings with little variations during the entire sleep; (3) Indeterminate: Frequent fluctuation within 4% range regardless of level of saturation. Significant oxygen saturation change is defined as a drop in oxygen saturation of greater or equal to 4% and to a level of 90% or below. Each series of changes represents an apnea episode.

Based on the pulse oximetry data (ODI) the blower would modify its output for treatment. For example, if the pulse oximetry data showed a positive indication of apnea events it would either turn on and begin delivery pressure or it would increase its pressure until the pulse oximetry data was indeterminate or negative. The blower would continue this process on an ongoing or periodically responding manner throughout the sleep period. This would achieve an APAP (Automatically adjusting Positive Airway Pressure) without the need to use conventional flow and pressure data.

The processing of the CPAP system may be made more robust using the following refinement criteria for the oximetry data, indicating an apnea event:
   SpO2 drops by 4% from the base line and is at or below 90%.
   SpO2 drops by a set amount (2%, 3% or 4%) for at least 10 s and the rate is >0.1%/s. Also, within one minute, SpO2 should return to within 1% of normal or recover by >150% of the set amount of the dip.
   The delta index is the average of absolute differences of SpO2 between consecutive 12-seconds interval. The delta index is compared against a set amount (2%, 3% or 4%). This approach also tracks the total amount of time spent below various levels (90%, 88%, 86%, 84%, 82%, and 80%).

A further evolution of the invention would be to have a CPAP blower also have a pulse oximetry processor built in. This would eliminate the need for an extra standalone electronics component and would make communication and the processing of pulse oximetry data more direct. Schematics of various systems are shown in FIGS. 2A-2D. FIG.

Figure 2A:
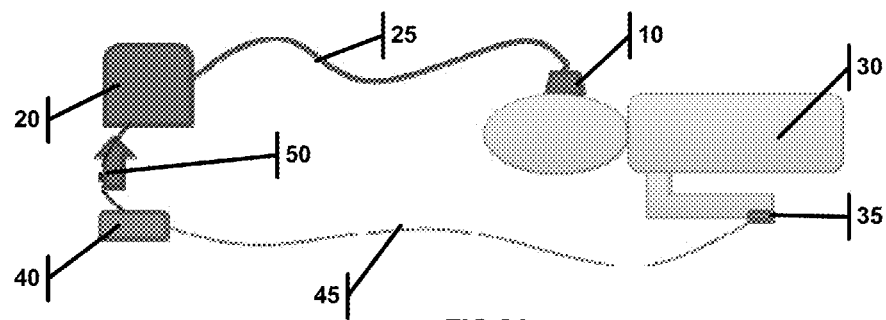
FIG. 2A illustrates a CPAP system that includes a wired oximetry sensor and a wired oximetry processor.
Figure 2B:
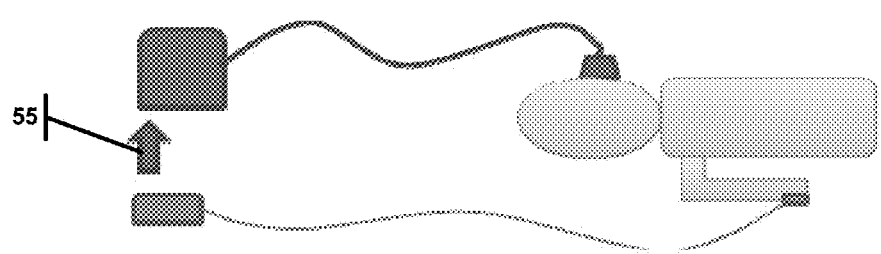
FIG. 2B illustrates a CPAP system that includes a wired oximetry sensor and a wireless oximetry processor.
Figure 2C:
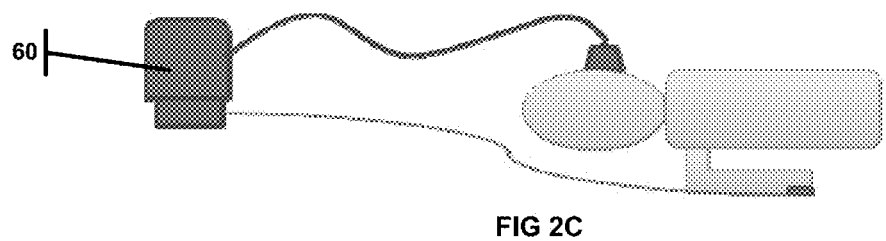
FIG. 2C illustrates a CPAP system that includes a blower with an integrated oximetry processor.
Figure 2D:
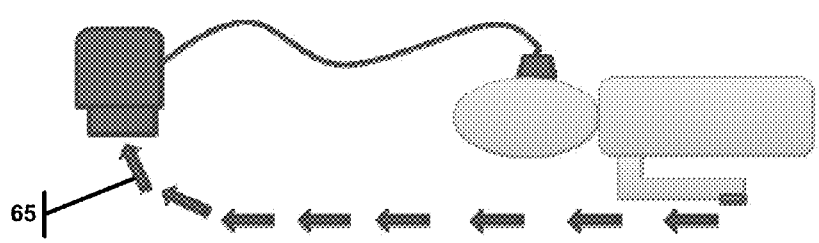
FIG. 2D illustrates a CPAP system that includes a wireless oximetry sensor.

2A shows a blower 20 providing positive pressure via a hose 25 to a mask 10. The blower is working in conjunction with pulse oximetry sensor 35 attached the finger of a patient 30. A oximeter proceeor 40 is connected via a wire 45 to the oximeter sensor and the processor 40 is also connected via a wire 50 to the blower. FIG. 2B shows a blower working in conjunction with pulse oximetry via a wireless communication 55. FIG. 2C shows a blower integrated with the pulse oximetry processor 60. FIG. 2D shows a blower with the integrated pulse oximetry processor using wireless connection 65 from the pulse oximetry sensor.

Figure 3A:
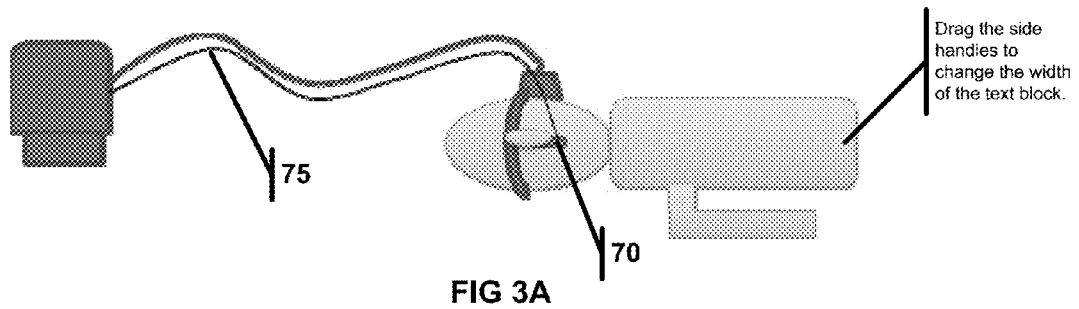
FIG. 3A illustrates a CPAP system that includes a mask with an integrated wired oximetry sensor.
Figure 3B:
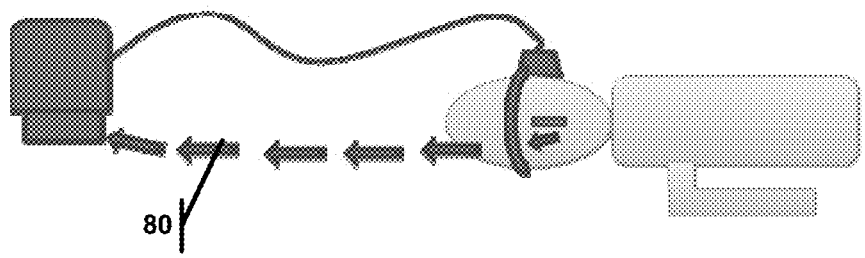
FIG. 3B illustrates a CPAP system that includes a mask with an integrated wireless oximetry sensor.

Regarding the measurement of pulse oximetry. As described previously, the measurement device was worn on the finger. There are, however, additional conventional sensors that can be worn in alternative ways for example a finger, hand, toe; foot or ear sensor. It would be useful to incorporate the pulse oximetry sensor on a component of the CPAP treatment mask or headgear. By way of example the ear could be a useful choice and would be a reasonable location for a headgear residing probe to be positioned. Currently pulse oximetry can be measured on the ear. Such a sensor can be incorporated into a mask 70 such as shown in FIG. 3A which has a wired connection 75 with the mask (which can run alongside with the hose or incorporated into the hose). Alternatively, as shown in FIG. 3B a wireless sensor and connection 80 may be use, which would may have the additional benefit of permitting a more generic hose to be used—i.e., a special hose with an incorporated wiring for the sensor need not be used.

Additionally, the processing of the CPAP system may be made more robust using the clinical scoring information described in the literature to augment its findings. Below are the clinical scoring items that each receives a point if present. A total score of three plus the pulse oximetry data represents a feasible way to detect apnea:

1. LOUD AND HABITUAL SNORING: this could be addressed by a simple yes/no response inputted from a physician or the user. Additionally a microphone in the mask or box could give the score
2. INTERRUPTED BREATHING: this could be monitored with an analysis of breathing sound, a movement sensor on the user's chest, a simple monitoring of box flow (in particular with the latest embodiment of the FRESCA mask, flow through the mask stops during exhalation and apnea so the pace of breathing would be easy to monitor at the box with a flow sensor monitoring gross flow data)
3. EXCESSIVE DAYTIME SLEEPINESS: this could be addressed by a simple yes/no response inputted from a physician or the user.
4. BODY MASS INDEX GREATER THAN 25: this could be addressed by a simple yes/no response inputted from a physician or the user.
5. USE OF HYPOTENSIVE MEDICATIONS OR BLOOD PRESSURE GREATER OR EQUAL TO 140/90: this could be addressed by a simple yes/no response inputted from a physician or the user.

Apnea can be the result of the airway collapsing (obstructive). It may also be the result of the brain not sending a signal to breathe correctly (central). In pure central sleep apnea, the brain's respiratory control centers are imbalanced during sleep. Blood levels of carbon dioxide, and the neurological feedback mechanism that monitors the levels do not react quickly enough to maintain an even respiratory rate, with the entire system cycling between apnea and hyperpnea, even during wakefulness. The sleeper stops breathing for up to two minutes and then starts again. There is no effort made to breathe during the pause in breathing: there are no chest movements and no struggling. After the episode of apnea, breathing may be faster (hyperpnea) for a period of time, a compensatory mechanism to blow off retained waste gases and absorb more oxygen. There are symptoms that one can find for the two different types of sleep apnea (central versus obstructive) as follows.

It would be useful to differentiate the apnea sleep disorders between Obstructive and Central. The following reference demonstrates the ability to make the differentiation: *Detection of Sleep Disordered Breathing and Its Central/ Obstructive Character Using Nasal Cannula and Finger Pulse Oximeter*; Dirk Sommermeyer, Ph.D., Ding Zou, M.D., Ph.D., Ludger Grote, M.D., Ph.D., and Jan Hedner, M.D., Ph.D. This reported concluded: "Automatic analysis based on routine pulse oximetry alone may be used to detect sleep disordered breathing with accuracy. In addition, the combination of photoplethysmographic signals with a nasal flow signal provides an accurate distinction between obstructive and central apneic events during sleep."

Figure 4:
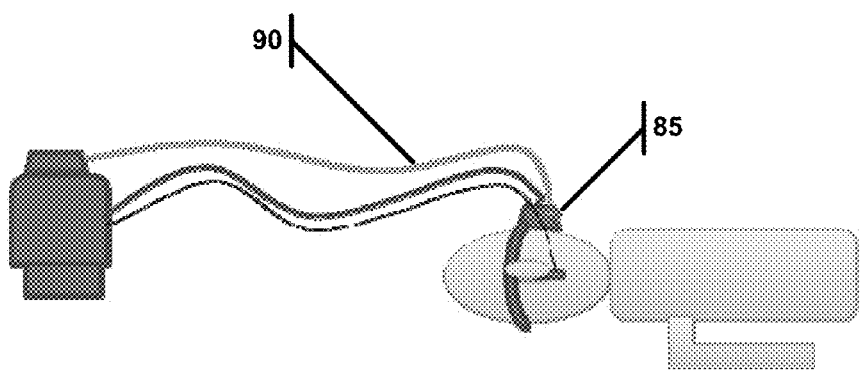
FIG. 4 illustrates a CPAP system that includes a mask with an integrated wired oximetry sensor and wired nasal air flow sensor.
Figure 5:
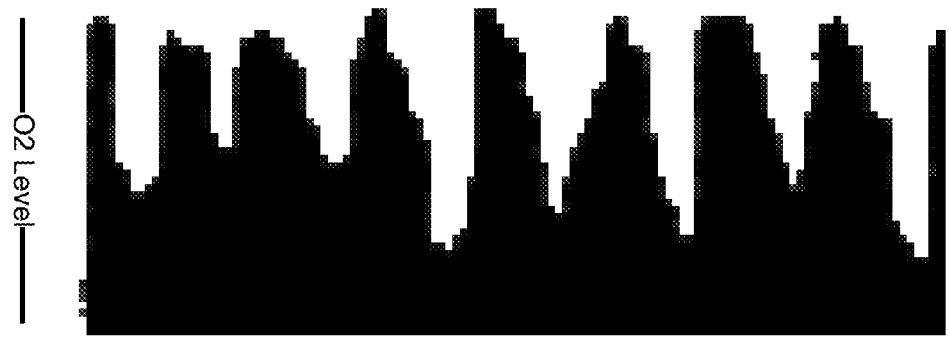
FIG. 5 illustrates blood oxygenation graphs over time that may indicate an apnea event.
Figure 5:
Figure 5:
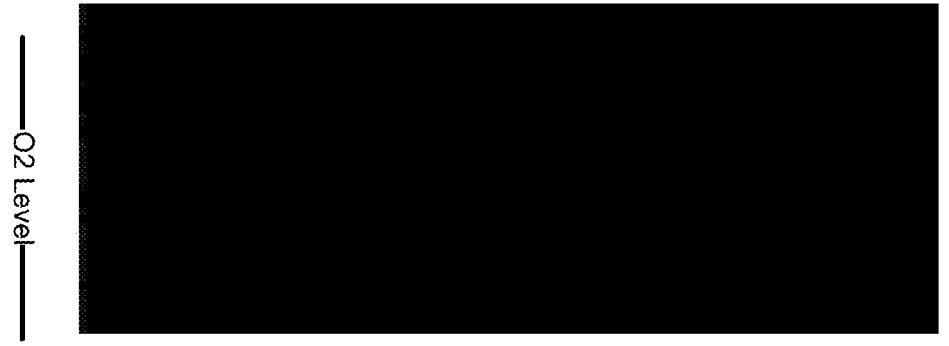

Incorporating a nasal airflow sensor in the sleep apnea system to work in conjunction with the pulse oximetry embodiments described above could be used to differentiate the modalities of sleep apnea. FIG. 4 shows a blower built with a pulse oximetry processor using wired signal from the pulse oximetry sensor that is part of the CPAP mask and interfacing with a useful location on the patient such as the earlobe additionally a nasal air flow sensor has been incorporated in the mask 85 with a wired connection 90 to an associated processor combined in the blower. The nasal airflow sensor may also have a wireless connection (not shown).

Traditionally, thermal devices such as thermistors or thermocouples have been used in the detection of sleep disordered breathing. The signal produced is a surrogate for actual patient airflow. It is proposed in this aspect of the invention that this sort of sensor is incorporated to measure nasal airflow. This is meant by way of example, but is not intended to limit other flow sensors from accomplishing the same function. Additionally the schematic above shows a wired system. It is also considered in this invention that the pulse oximetry and nasal airflow signals could be wireless.

Figure 9:
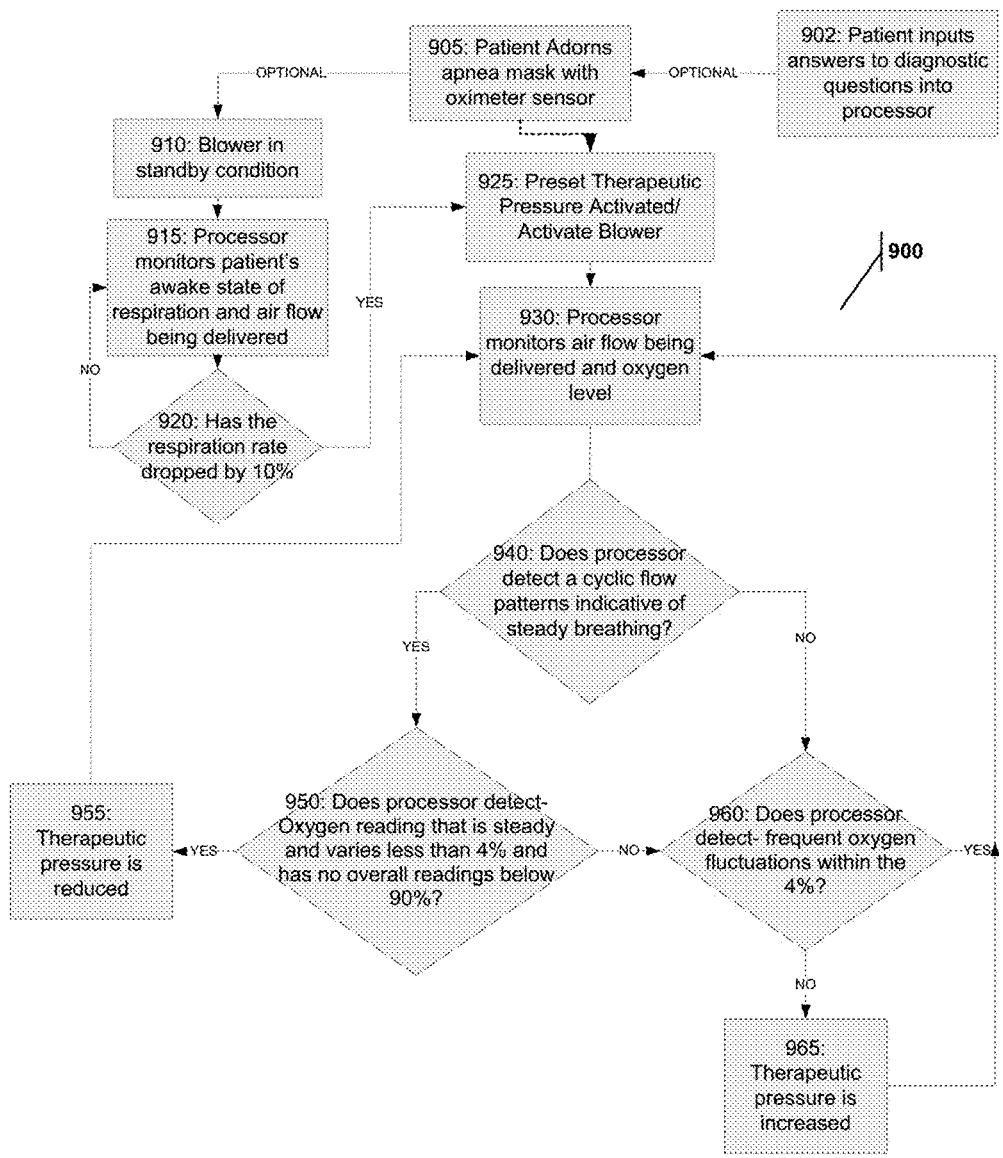
FIG. 9 is a flowchart for the processor using the oximeter data.

FIG. 9 illustrates a method using the oximetry data from the sensor (and optionally from the nasal flow sensor) to refine a sleep apnea system. The blower may be connected to the processors as described above, and by measuring the pressure in the hose, the processor can detect whether the patient is breathing. For example, in U.S. application Ser. No. 14/930,284 titled "APPARATUS, SYSTEMS, AND METHODS FOR TREATING OBSTRUCTIVE SLEEP APNEA" filed on Nov. 2, 2015, discloses an apnea mask with a valve opening pressure that is adjusted by the amount of pressure applied by the blower through the hose; thus by monitoring the pressure and airflow in the hose, the processor can determine whether the patient is causing the valve to open, which indicates that the patient is breathing. This determination can be verified by using the optional nasal flow sensor that may be included in the mask.

The patient or the medical professional caring for the patient would set a therapeutic pressure that the patient needs to treat the OSA. Optionally, the method 900 may ask the patient to input several answers to diagnostics questions at step 902. These may include: (1) do they habitually snore; (2) do they have excessive daytime sleepiness; (3) do they have a BMI of greater than 25; and (4) do they use hypotensive medications or have blood pressure greater or equal to 140/90. The patient's answers are feed into the processor, which can use this information in conjunction with sensor data to refine the therapeutic treatment for the OSA. The patient then at step 905 adorns the apnea mask with the oximeter sensor and attempts to fall asleep. Optionally, the blower may be placed in a standby condition (step 910) while the processor monitors the patients awake state of respiration and air flow (steps 910, 915). This monitoring may be assisted by a nasal airflow sensor discussed above. Once the processor detects a reduction in the respiration rate at step 920, then the blower can be activated at the therapeutic pressure (step 925). The amount of respiration rate reduction may be adjusted depending on the patient, but a reasonable reduction rate is about 10%. The method 900 may not need to monitor the patient's awake respiration and instead proceed from step 905 directly to step 925 and activate the blower. It should be noted that the therapeutic pressure need to be reached immediately upon activating the blower in step 925; rather the pressure may be gradually increased until the therapeutic pressure is reached. Such a method is disclosed in U.S. application Ser. No. 14/930,284 titled "APPARATUS, SYSTEMS, AND METHODS FOR TREATING OBSTRUCTIVE SLEEP APNEA" filed on Nov. 2, 2015.

The processor at step 930 monitors the airflow and pressure in the hose (and optionally in the nasal air flow sensor), as well as the oxygen level from the oximeter sensor. If the processor detects a cyclic flow pattern that is indicative of steady breathing at step 940, then the processor determines whether the oxygen readings are steady and vary less than 4% with no overall readings below 90% at step 950. A cyclic flow pattern may be identified by measuring the flow rate from the blower. As described above, the unique mask disclosed in U.S. application Ser. No. 14/930,284 titled "APPARATUS, SYSTEMS, AND METHODS FOR TREATING OBSTRUCTIVE SLEEP APNEA" filed on Nov. 2, 2015, allows for such a measurement. Specifically, upon inhalation by the patient the flowrate through the hose will be at a maximum and during exhalation, the flowrate will be near zero. Measuring these flowrate fluctuations, the processor can determine the respiration rate of the patient. So, for example, the processor may look for a second of high flow (inspiration) followed by a couple of seconds of low flow (transition) and followed by three seconds of no flow or even trace negative flow (exhalation). This could represent a common breath where inspiration is quicker and expiration is elongated. It is anticipated the processor would monitor this pattern for numerous cycles and generate an average or best fit curve that would then be computed as the cyclic pattern. An apneic event could be a prolonged period of low flow delivered from the blower. For example 5-10 seconds of low/no flow would be a good indicator of apnea. Hypopnea would be a cyclic flow pattern as described above but with about a 70% reduction in the anticipated blower supplied flow rate or a cyclic breathing pattern that increased in time by 30% or more.

If the answers to steps 940 and 950 are both affirmative, the processor can conclude that there has been no apnea event and may reduce the therapeutic pressure at step 955, and the processor continues to monitor at step 930. It should be noted that this method works optimally with an apnea mask that allows a patient to breathe without resistance (or extremely low resistance) even when the mask is not being provided an airflow from the blower. Such a mask is disclosed in U.S. application Ser. No. 14/930,284 titled "APPARATUS, SYSTEMS, AND METHODS FOR TREATING OBSTRUCTIVE SLEEP APNEA" filed on Nov. 2, 2015. This type of mask allows the patient to adorn the mask without having to immediately turn on the blower, and allows the method 900 to monitor the patient in the awake state, while the blower is in standby (steps 910-920). The mask also allows the method 900 to reduce the therapeutic pressure step 955 without choking the patient off from oxygen during sleep. In fact, by adjusting the therapeutic pressure based on the sensed data using the unique apnea mask, it makes the patient more comfortable because the pneumatic splint is used only when necessary; otherwise the patient breathes on his/her own.

Turning back to method 900, if at step 940 the processor detects a cyclic flow pattern that is not indicative of steady breathing and determines that the oxygen fluctuations are within a 4% band (step 960), then the processor cannot determine if there is an apnea even (indeterminate) and the method 900 leaves the therapeutic pressure unchanged. If however, the answer to step 940 is negative and the processor detects fluctuations outside the 4% band then this indicated an apnea event and the therapeutic pressure is increased at step 965.

Returning once again to step 950, if the answer is negative (i.e., determines whether the oxygen readings are not steady or vary more than 4% with overall readings below 90%), then the method 900 continues to step 960 discussed above.

5.3 Composite Construction Air Delivery Hose for Use with CPAP Treatment

The hose connects to the blower which allows air to enter into the mask. The pressurized air essentially inflates the airway to keep it open preventing collapse during breathing. Typically, air flow for CPAP ranges from 100-200 L/min at a corresponding pressure range of 4-20 CM-H2O. This high flow rate makes breathing feel quite uncomfortable for many patients and requires a large and cumbersome hose measuring about 22 mm (~0.86 in) diameter. Additionally, the high required flow rates of CPAP often causes discomfort during exhalation due to increased resistance, as well as nasal dryness, dry mouth, ear pain, rhinitis, abdominal bloating and/or headaches. Typically, a user requires a humidification machine to prevent some of the side effects of the high flow rate.

FRESCA Medical overcomes the shortcomings of conventional CPAP by developing a low flow rate CPAP device, described in the patent applications listed above. The FRESCA Medical device requires flow rates ~10× lower (10-25 L/min) to maintain pressure between 4-20 CM-H2O in order to "splint" the airway. As a result, the hose necessary for the improved device has a diameter of 8 mm as compared to the 22 mm traditional hose. A disclosure of such a hose is found in U.S. patent application Ser. No. 14/278,587, filed May 15, 2014, titled "Auto-Feedback Valve For A sleep Apnea Device," which is incorporated herein by reference.

Figure 8:
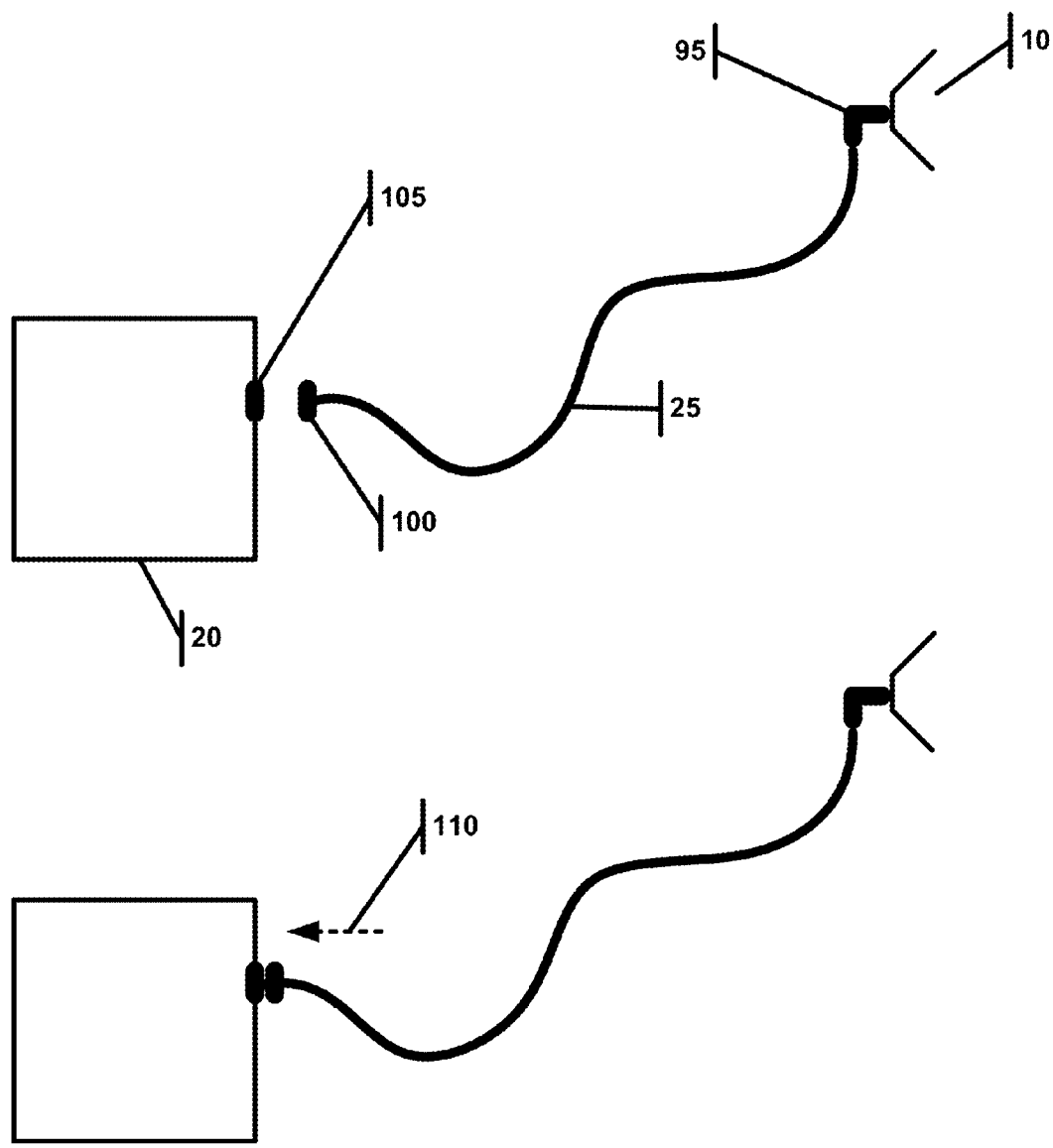
FIG. 8 illustrates a CPAP system with a hose that has an elbow and a magnetically induced blower connection.

As shown in FIG. 8, the hose is comprised of three main components: the hose 25, elbow mask connection 95, and hose blower connector 100. The hose is a composite silicon-coated braided tube that is lightweight, has excellent flexibility, good flow rates, strong crush resistance, and high durability. The elbow is an angled piece that can detach and attach to the mask while being rotatable and allowing directionality of the hose as it exits the mask. Lastly, the blower connector may use a magnet to connect to the air-pressurizing device for easy quick connection and disconnection. These and other improvements discussed later will help improve patient compliance and overall treatment of sleep apnea.

The hose performance relative to its wall thickness to cross sectional area distinguishes it from prior hoses. While the specifications of a hose is affected by material, design, size, and structure, the wall thickness to cross sectional area is a good performance indicator of the hose. Having a lower wall thickness to cross sectional area ratio allows for a more lightweight and flexible hose while maintaining a large cross sectional area for high flow rates. The hose is able to achieve a low wall thickness to cross sectional area ratio of 0.264. Below is a table of the performance characteristics.

TABLE 1

Performance Characteristics of the Hose

| Characteristic | Value |
| --- | --- |
| Wall thickness/cross sectional area ratio | 0.264 |
| Weight/Length ratio | 0.111 oz/ft |
| Bend Radius | ~0.5" without kinking |
| Droop percent (how much the hose bends under its own weight with a 1 [ft] section unsupported and extended off a horizontal plane) | ~88% droop distance over a 1 ft length (the amount the hose vertically displaces at the tip divided by 1 ft) |
| Stretch | ~150% (a one foot sample hung vertically with a 500 gm weight elongates to 150% its initial length) |
| Crush distance/ID percentage | ~32% of ID crushed for 5.5 lbf applied over a 2 inch length |

The hose has a low weight/length ratio, which is less cumbersome and more convenient for the user (Table 1). In addition, the small bend radius and high droop percentage signifies a high flexibility of the hose, which allows for an increased range of motion for the user. Lastly, the hose has the ability to readily stretch with tensile loads. This is a useful feature for decoupling tensile loads due to force on the hose. Additionally, as indicated in the table below, while stretching the hose affects flow rates, the pressure is unaffected even at 20% stretch lengths. Maintaining pressure while stretching the hose means fewer problems with operation—in situations where the user stretches the hose, the functionality of the CPAP therapy will not be impeded.

To clarify further, traditional CPAP systems utilize a mask with an intended leak. Pressure is created by excess air flow creating a back pressure against the intended leak. Small variations in air flow directly affect the pressure developed in the mask. Therefore traditional CPAP masks are highly reliant on receiving a particular amount of airflow to achieve pressure. The FRESCA mask, disclosed in the patent applications listed above, uses an expiratory valve that governs exhalation resistance. Therefore it is not as susceptible to changes of air flow to achieve pressure. As long as enough flow is being delivered to counteract any non-intended leak from the mask, the FRESCA system can be pressurized. Because of this the FRESCA system can tolerate a hose that stretches and necks down.

TABLE 2

Stretch vs. Flow Rate

| Stretch percent | CPAP Pressure | Initial Flow Rate (L/Min) | Stretched Flow Rate (L/Min) | Percent Change |
| --- | --- | --- | --- | --- |
| 10% | 4 | 17.6 | 15.13 | −14.0% |
|  | 12 | 30.1 | 25.4 | −15.6% |
|  | 20 | 39 | 32.2 | −17.4% |
| 20% | 4 | 17.6 | 12.35 | −29.8% |
|  | 12 | 30.1 | 21.6 | −28.2% |
|  | 20 | 39 | 27.5 | −29.5% |

TABLE 3

Stretch vs. Pressure

| Stretch percent | CPAP Pressure | Initial Measured Pressure (Cm—H2O) | Stretched Measured Pressure (Cm—H2O) | Percent Change |
| --- | --- | --- | --- | --- |
| 10% | 4 | 3.8 | 3.8 | 0% |
|  | 12 | 11.8 | 11.8 | 0% |
|  | 20 | 19.8 | 19.8 | 0% |
| 20% | 4 | 3.8 | 3.8 | 0% |
|  | 12 | 11.8 | 11.8 | 0% |
|  | 20 | 19.8 | 19.8 | 0% |

In comparison, there are many examples of braided hoses in commercial use. The performance characteristics of typical braided hoses, however, are not as good compared to the novel hose described herein. For comparison, we analyzed two types of common braided hoses—integrated braided hoses and externally braided hoses.

Figure 6:
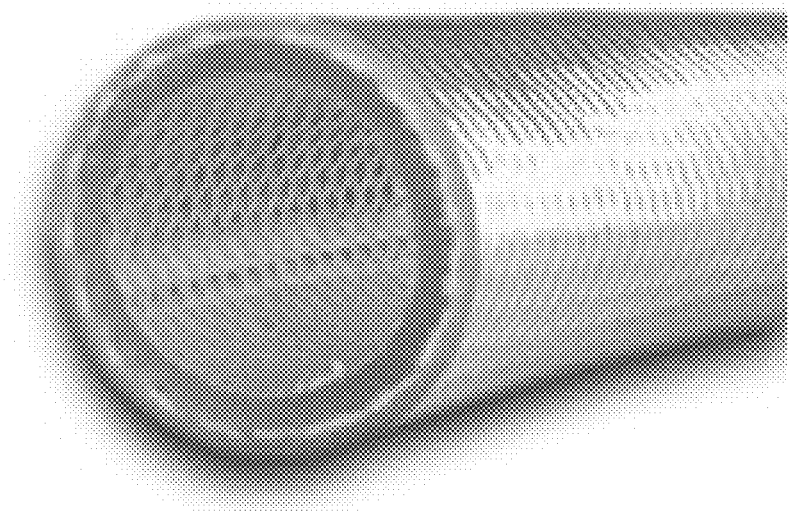
FIG. 6 is a photo of an internally braided hose.

FIG. 6 shows a high pressure PVC hose with an integrated braid. The sample used for comparison was a high pressure PVC tubing with an inner diameter of 0.25" and an outer diameter of 0.50". In this conventional construction, its wall thickness to cross sectional area ratio is 2.54 compared to FRESCA's invention of 0.264; nearly a 10 fold difference (Table 4). Below are the performance characteristics of the PVC hose. The PVC hose is relatively heavy, not particularly flexible, has poor stretch, and not intended to provide a supple feel. These characteristics make the hose less than ideal for CPAP users who require both comfort and functionality.

TABLE 4

Performance Characteristics of the Integrated Braided PVC Hose

| Characteristic | Value |
| --- | --- |
| Wall thickness/cross sectional area ratio | 2.54 |
| Weight/Length ratio | 1.28 oz/ft |
| Bend Radius | ~1.7 in. without kinking |
| Droop percent | ~36% droop distance over a 1 ft length |
| Stretch | ~0% (1 ft section loaded with 500 gm) |
| Crush distance/ID percentage | ~23% of ID crushed for 5.5 lbf applied over a 2 inch length |

Figure 7:
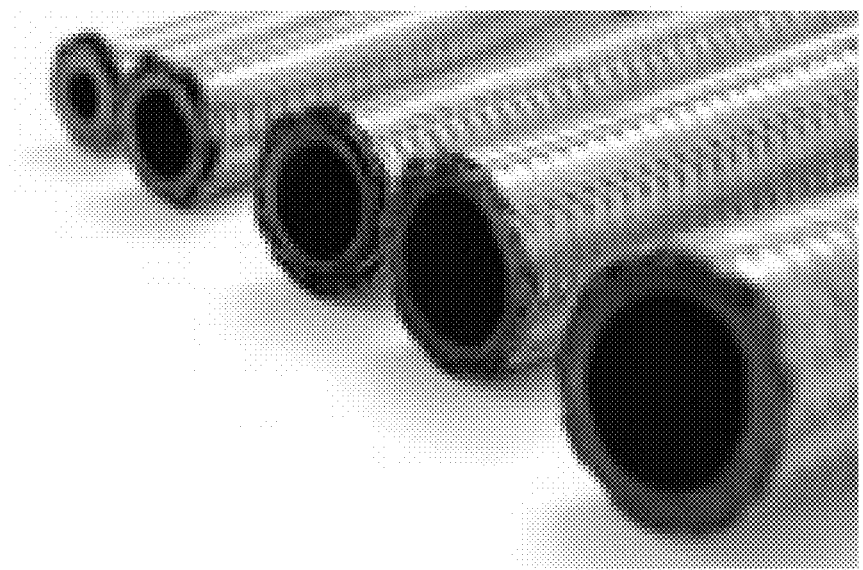
FIG. 7 is a photo of an externally braided hose.

Another example is a high-pressure hose with an external braid cladding over an internal tube. The sample used for comparison had an inner diameter of 0.200" and an outer diameter of 0.300" and is shown in FIG. 7. Its wall thickness to cross sectional area ratio is 1.59 compared to FRESCA's invention of 0.264; nearly a 6 fold difference. (See Table 5). Below are the performance characteristics of the externally braided hose. Again, the externally braided hose is relatively heavy, not particularly flexible, has poor stretch, and not intended to provide a supple feel. The poor characteristics of other types of braided hoses contrasts sharply with the novel properties of the FRESCA hose disclosed herein.

TABLE 5

Performance Characteristics of the Externally Braided Hose

| Characteristic | Value |
| --- | --- |
| Wall thickness/cross sectional area ratio | 1.59 |
| Weight/Length ratio | 0.32 oz/ft |
| Bend Radius | ~0.7" without kinking |
| Droop percent | ~71% droop distance over a 1 ft length |
| Stretch | ~7% (1 ft section loaded with 500 gm) |
| Crush distance/ID percentage | ~35% of ID crushed for 5.5 lbf applied over a 2 inch length |

The superior performance of the hose has multiple benefits for a CPAP user. A typical CPAP user is attempting to sleep while wearing a mask for CPAP treatment. Due to the sleep apnea condition, CPAP patients intrinsically have issues with obtaining proper sleep. Any additional external distractions further prevent the user from obtaining proper sleep. To that end, user perception, user interaction, and user comfort is just as important as the functional performance of the FRESCA hose.

Overall, the novel engineering characteristics of the FRESCA hose assembly will greatly improve the CPAP user experience. The FRESCA hose mitigates distractions in size, weight, flexibility, and tug as compared to a conventional CPAP hose. First, the small size of the FRESCA hose is much less of a distraction for the user. Being approximately a third of the diameter of a typical CPAP hose reduces its visual and physical presence. A conventional CPAP hose is typically uncomfortable to sleep on due to its large size. If a user lies on the FRESCA hose, they may not even notice that it is there due to its small size. Also, for travel and storage a user with a FRESCA hose won't need as much space compared to a conventional CPAP hose.

Second, the weight of the hose can affect comfort during sleeping. The FRESCA hose, including a 6 ft hose, the box connector, and the mask connector, weighs only 0.914 oz whereas a conventional 6 ft CPAP hose has a weight of 4.3 oz, nearly five times heavier. The FRESCA hose is less cumbersome compared to a conventional CPAP hose, which is more convenient for the user. A lighter hose has less pull on the mask.

Third, flexibility of the hose affects the range of motion of the hose. The FRESCA hose has a bend radius of 0.5 in. compared with a conventional hose that has a bend radius of ~1 in. The greater flexibility allows for an increased range of motion for the user. For example, users that move in their sleep can find it distracting when a typical CPAP hose does not conform to the user's motion. The FRESCA hose has greater flexibility, which allows for more movement of the hose, conforming better to the user's movement.

Finally, when the hose tugs on the mask or box, it can be distracting to the user during sleep. The FRESCA hose can elongate by 50% percent at a small loading of 1.1 lbs while still providing 90% of its pressure. In comparison, a conventional CPAP hose can barely stretch at all. Having a high elongation is useful in that the hose decouples tensile loads from the mask and box. For example, conventional CPAP hoses provide nearly a 1:1 force transmission from hose to box or mask due to their poor elongation. This makes them prone to dislodging the mask or applying a distracting tug or drag to a user intent on sleeping. In contrast, the FRESCA hose will stretch, mitigating a distracting tug or drag on the user.

An additional benefit of the FRESCA hose assembly is a novel magnetic connection to the blower, as shown in FIG. 8. Conventional CPAP hoses have a rubber boot that requires one to manually slip over a post in order to attach/detach. The FRESCA hose has a "doughnut" shaped magnetic connection on the hose 100 that will automatically attach to a blower magnet assembly 105 when the hose is in close proximity to the blower 20. The magnetic connection creates a simple quick attach/detach coupling system, which has enough force 110 to prevent users from accidently pulling off the connection. For example, consider a drowsy user, in dim or non-lit room that needs to couple or decouple the hose from the blower. The use of a "doughnut" magnetic connection allows the hose to be attached without any orientation dependency (this is an additional feature of the FRESCA mask, in that it may use a single lumen hose, those hose connection orientation is not critical). Additionally there is no need to perform a particular attachment or detachment step such as press fitting a rubber boot, twisting in a particular direction, or activating a pinch clip. The FRESCA magnetic connector (100, 105) only needs to be with proximity to self-align and self-connect. Furthermore, for removal the user can pull the connector off in a linear fashion or gently "bend/cantilever" it off in a transverse fashion.

Figure 8A:
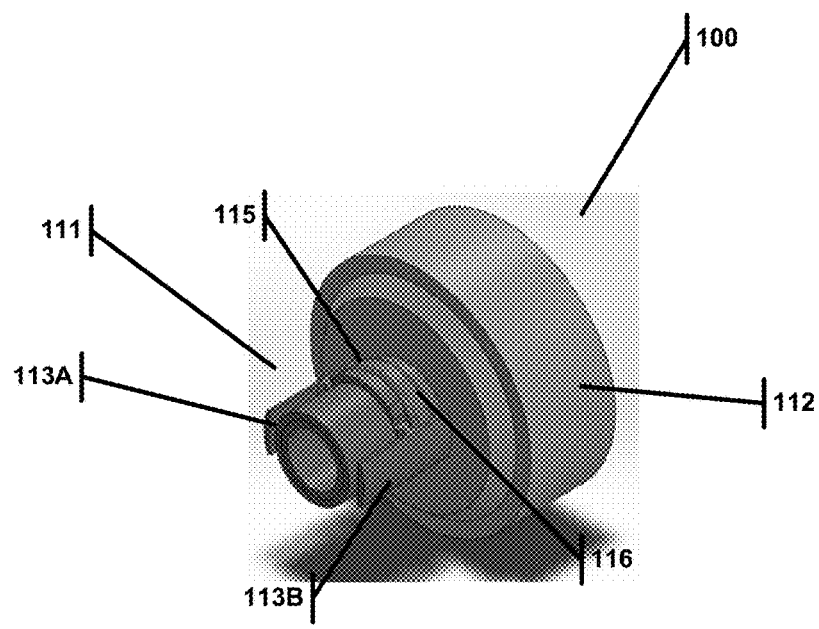
FIG. 8A is an isometric view of a magnetic connector.

FIGS. 8A and B demonstrate one possible embodiment of such a magnetic connection between the hose assembly 100 and the blower assembly 105. On the left side is a hose assembly connector 111, and on the right side is a blower assembly connector 112. The blower assembly 105 features a post 115, and the hose connector 100 has one or more hinges (113a, 113b) that may latch onto the post 115. The post 115 may extend outwardly from the blower assembly 105 and may include a channel/collar 116 for the entire circumference of the post 115, such that the connectors (111, 112) can rotate freely relative to each other.

The hinges (113a, 113b) may include a long side 120 and a short side 125, where the short side 125 engages with the channel or collar 116. Once attached, the hinges (113a, 113b) will prevent the hose connector 100 from detaching from the blower assembly 105. To facilitate the connection the end 130 of the hinges may be angled so that the end easily attaches to the post 115 by applying minimal push force. The connection may be aided by a magnet 135 that allows the hose assembly connection 111 to self-connect due to the magnetic force and to have a stronger pull force to prevent accidental disconnections and reduce any leakage. The connector 100 can freely rotate along the post of the blower magnetic assembly 105. Thus, when the hose connector 100 rotates, and the short side of the hinge 125 are latched on to the collar or channel 116, the connection 110 between the hose assembly 100 and the blower assembly 105 remains secure. When the hinges (113a, 113b) on the hose connector 100 are pressed by the user on the long side 120, the short side 125 will move away from the channel/collar 116 of the blower magnetic assembly 105.

Similarly, a rotatable hinge connector can also be used for the connection between the sleep apnea mask 10 and the hose 25 at the mask connection 95. With this novel type of magnetic connection between components of a CPAP system, the hose 25 would be able to rotate freely at both the mask connection 95 and the blower assembly connection 110. In the prior art, since the blower box end connection does not rotate, the long hose can end up building torque tension as the user or the blower moves, which results in coiling of the hose. The resulting problem is that a coiling hose can lead to kinks, decreased flexibility, decreased range of motion, and shorter effective length of the hose. These factors often lead to user issues, such as accidentally pulling the CPAP blower off the nightstand during sleep, dislodging the mask from the user's face, and limited airflow and loss of therapeutic effects of the CPAP system. The present embodiments, by presenting this novel magnetic connection that may be used at both ends of the hose 25, prevents the hose 25 from coiling, reducing or eliminating the undesirable effects associated with a coiling hose. With the magnetic connection disclosed by the present invention, every area along the hose 25 has the ability to rotate, preventing the buildup of torque tension that leads to a coiling hose. The system disclosed herein thus offers the advantages of reduced likelihood of accidents and reduced likelihood of losing airflow due to a coiled hose compared to prior art.

Figure 8B:
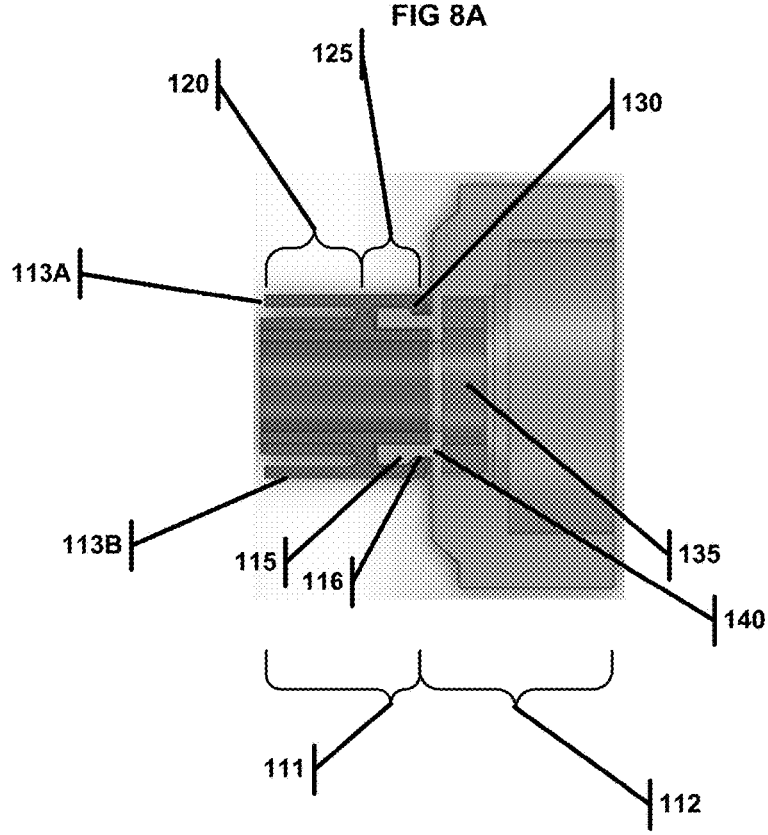
FIG. 8B is a cross-sectional view of the magnetic connector of FIG. 8A.
Figure 10A:
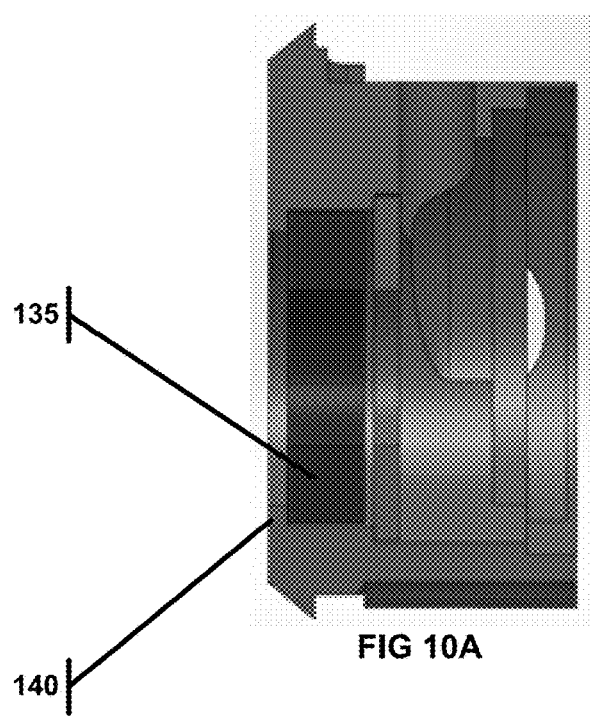
FIG. 10A is a cross-sectional view of another embodiment of a magnetic connector.
Figure 10B:
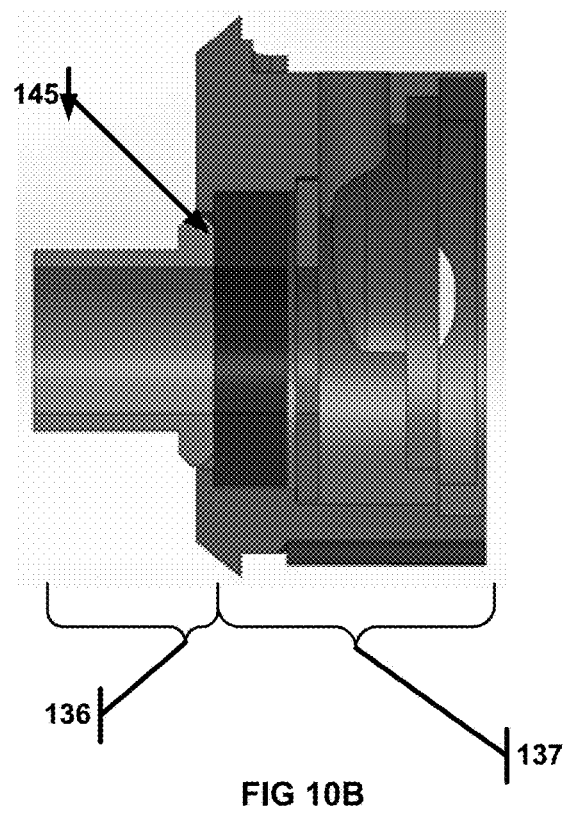
FIG. 10B is a cross-sectional view of the connector of FIG. 10A physically connected to a hose assembly connector.

FIGS. 10A and 10B illustrate yet another embodiment of such a magnetic connection between the hose assembly and the blower assembly. On the left side is a hose assembly connector 136, and on the right side is a blower assembly connector 137. The magnet 135 is housed in the blower assembly connector 137, and is retained within the housing by a retainer 140 that keep the magnet 135 from separating from the blower assembly connector. This retainer 140 is also shown in FIG. 8B and performs the same function in that embodiment. The retainer 140 does not, however, prevent the movement of the magnet 135 within the housing. Rather the magnet 135 is allowed a little bit of room within the housing so that the magnet can freely rotate. The hose assembly connector 136 is comprised of steel that forms a magnetic connection with the magnet 135. As shown in FIG. 10B the hose assembly connector 136 comes into physical contact (shown by arrow 145) with the magnet 136. Therefore when the hose imparts a rotational force on the hose assembly connector 136, the physical connection (arrow 145) will cause the magnet to rotate relative to the retainer 140.

Figure 11:
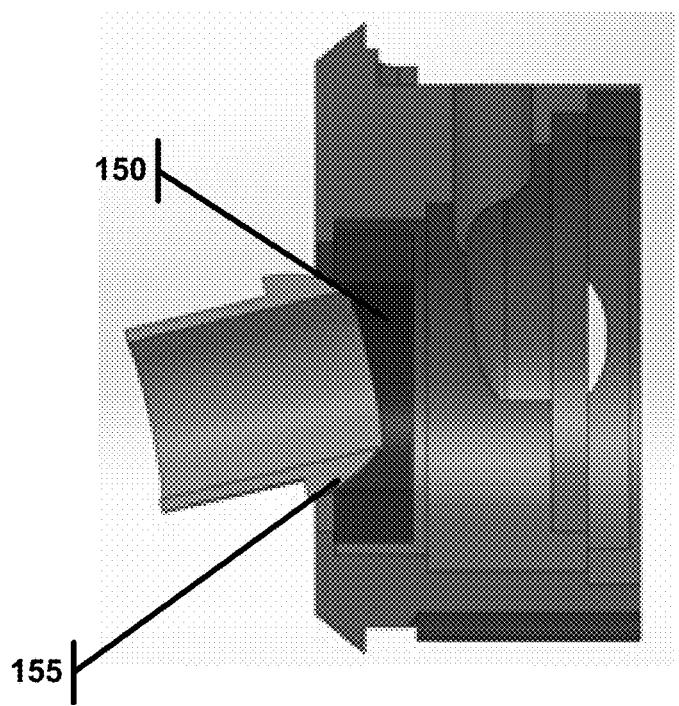
FIG. 11 shows a tapered hose assembly connector.

The magnet 135 may be doughnut-shaped with an interior hole 150 and the end of the hose assembly connector 136 may be tapered or "ball shaped" 155, and the tapered end 155 may enter the interior hole 150 partially or completely as shown in FIG. 11. This unique design allows for not only rotational movement of the hose assembly connector 136 relative to the blower assembly connector 137, but also angular movement.

This hose is made by heat setting a PET braid on a 0.312 in. diameter stainless steel mandrel for 30 min at 140° C. The material is allowed to cool and loaded on a 0.312 in. diameter PTFE mandrel. It is dip coated in silicone dispersion and air cured for 1 hr. After which it is de-mandreled, hung vertically, and an internal coating of dispersion is poured though and through the lumen. Below in Table 6 is the specification of the braid, dispersion, and performance specifications:

TABLE 6

| | |
|---|---|
| Monofilament | 0.010" PET |
| Color | Black |
| Carriers | 32 elements |
| Pattern | Regular (Full load = 1 over 2 under 2) |
| Pick Count | 17 |
| ID | ~0.310" (after heat set) |
| OD | ~0.350" |
| Thickness | ~0.020" (wall thickness measured with calipers) |
| Length | 6 feet |
| Weight | 0.668 oz (0.914 oz with mag connect, elbow, both collars - This is the weight of the hose assembly) |

TABLE 6-continued

| | |
|---|---|
| Dip | MED 16-6606 or MED 6-6606 (NuSil single part, air cure, silicone dispersion) |
| Bend Radius | ~0.5" without kinking |
| Stretch | ~50% (a 1[ft] sample hung vertically with a 500[gm] weight |
| Crush | ~0.1" distance over a 2 inch length up to 5.5 lbf |
| Droop | 10.5" droop for a 12" length |
| Flow rate | 10-25 L/min through the hose using a conventional CPAP blower box set correspondingly at 4-20[cm H2O] pressure |
| Wall thickness/cross sectional area ratio | 0.264 |
| Weight/Length ratio | 0.111 [oz/ft] (this is based off just the hose component and does not account for connectors) |

Any of the suitable technologies and materials set forth and incorporated herein may be used to implement various example aspects of the invention as would be apparent to one of skill in the art.

Although exemplary embodiments and applications of the invention have been described herein including as described above and shown in the included example Figures, there is no intention that the invention be limited to these exemplary embodiments and applications or to the manner in which the exemplary embodiments and applications operate or are described herein. Indeed, many variations and modifications to the exemplary embodiments are possible as would be apparent to a person of ordinary skill in the art. The invention may include any device, structure, method, or functionality, as long as the resulting device, system or method falls within the scope of one of the claims that are allowed by the patent office based on this or any related patent application.

The invention claimed is:

1. A sleep apnea treatment system comprising:
a hose with a hose magnetic assembly at an end of the hose;
a blower with a complementary blower magnetic assembly and a retainer that prevents the complementary blower magnetic assembly from separating from the blower, the complementary blower magnetic assembly constructed to freely rotate relative to the retainer, wherein the hose magnetic assembly experiences a magnetic attraction to the blower complementary magnetic assembly when the hose end is brought into close proximity to the blower, wherein the magnetic attraction is sufficiently strong enough to bring the hose end into contact with the blower;
the blower further adapted to produce a flow of pressurized air to the hose when the hose end is in contact with the blower; and
wherein the hose magnetic assembly and the complementary blower magnetic assembly further configured such that these two assemblies can rotate relative to the retainer and the hose can be attached without rotational orientation dependency.

2. The system of claim 1, wherein the blower magnetic assembly comprises a post extending outwardly along the entire circumference of the blower magnetic assembly.

3. The system of claim 2, wherein the hose magnetic assembly comprises at least one hinge with an end, and the post comprises a channel, wherein the hinge may engage with the channel securely mating the first hose magnetic assembly to the complementary blower magnetic assembly.

4. The system of claim 3, wherein hinge comprises a long side that may be pressed by a user to detach the first hose magnetic assembly from the complementary blower magnetic assembly.

5. The system of claim 1, wherein the hose is braided.

6. The system of claim 5, wherein the hose is coated in silicone.

7. The system of claim 1, further comprising:
 a second hose magnetic assembly at a second end of the hose; and
 a sleep apnea mask with a mask magnetic assembly complementary to the second hose magnetic assembly.

8. The system of claim 7, wherein the second hose magnetic assembly and the complementary mask magnetic assembly are constructed such that they can rotate freely relative to one another.

9. The system of claim 7, wherein the mask magnetic assembly comprises a post extending outwardly along the entire circumference of the blower magnetic assembly.

10. The system of claim 9, wherein the second hose magnetic assembly comprises at least one hinge with an end, and the post comprises a channel, wherein the hinge may engage with the channel securely mating the second hose magnetic assembly to the mask magnetic assembly.

11. The system of claim 10, wherein hinge comprises a long side that may be pressed by a user to detach the second hose magnetic assembly from the mask magnetic assembly.

12. The system of claim 1, comprising an oximeter sensor.

13. The system of claim 12, comprising a processor constructed to read a signal from the oximeter sensor.

14. The system of claim 13, comprising an airflow sensor, wherein the processor is constructed to read a signal from the airflow sensor.

15. The system of claim 14, wherein the processor is constructed to reduce the pressure of the flow of air from the blower, based on the signals the processor receives from the oximeter and airflow sensors.

16. The system of claim 14, wherein the airflow sensor is a nasal airflow sensor.

17. The system of claim 14, wherein the airflow sensor is located in the sleep apnea mask.

18. The system of claim 14, wherein the airflow sensor is located in the hose.

19. The system of claim 1, wherein the complementary blower magnetic assembly is doughnut-shaped with an interior hole and the hose magnetic assembly is constructed to enter the interior hole.

20. The sleep apnea treatment system comprising:
 a hose with a hose magnetic assembly at an end of the hose;
 a connector with a complementary blower magnetic assembly and a retainer that prevents the complementary blower magnetic assembly from separating from the connector, the complementary blower magnetic assembly constructed to freely rotate relative to the retainer, wherein the hose magnetic assembly experiences a magnetic attraction to the commentary magnetic assembly when the hose end is brought into close proximity to the connector, wherein the magnetic attraction is sufficiently strong enough to bring the end of the hose into contact with the connector; and
 wherein the hose magnetic assembly and the complementary magnetic assembly further configured such that these two assemblies can rotate relatively to the retainer and the hose can be attached without rotational orientation dependency.

21. The system of claim 20, wherein the complementary magnetic assembly is doughnut-shaped with an interior hole and the hose magnetic assembly is constructed to enter the interior hole.

22. The system of claim 20, wherein the hose magnetic assembly is metal and the complementary magnetic assembly is magnetic.

* * * * *